United States Patent [19]

Sirrenberg et al.

[11] Patent Number: 4,886,823
[45] Date of Patent: Dec. 12, 1989

[54] FURAZANYLUREA ACARICIDES

[75] Inventors: Wilhelm Sirrenberg, Sprockhoevel; Albrecht Marhold; Ulrike Wachendorff-Neumann, both of Leverkusen, all of Fed. Rep. of Germany

[73] Assignee: Bayer Aktiengesellschaft, Leverkusen, Fed. Rep. of Germany

[21] Appl. No.: 269,263

[22] Filed: Nov. 9, 1988

[30] Foreign Application Priority Data

Nov. 17, 1987 [DE] Fed. Rep. of Germany ....... 3738946

[51] Int. Cl.$^4$ .................... C07D 271/08; A01N 47/36
[52] U.S. Cl. ..................................... 514/364; 548/125
[58] Field of Search .......................... 548/125; 514/364

[56] References Cited

U.S. PATENT DOCUMENTS 4,699,916 10/1987 Sirrenberg ........................... 514/364
4,764,524 8/1988 Sirrenberg ........................... 514/364

FOREIGN PATENT DOCUMENTS 0132680 2/1985 European Pat. Off. ............ 548/125

Primary Examiner—Robert Gerstl
Attorney, Agent, or Firm—Sprung Horn Kramer & Woods

[57] ABSTRACT

Acaricidal 1-arylfurazanyl-3-(2-alkyl-4-halogenoalkoxyphenyl)-(thio)ureas of the formula

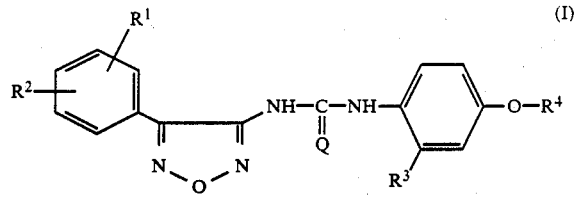

in which
Q stands for oxygen or sulphur,
$R^1$ stands for hydrogen, halogen, alkyl, halogenoalkyl, alkoxy, halogenoalkoxy, alkylthio or halogenoalkylthio, and
$R^2$ stands for hydrogen, halogen, alkyl or alkoxy, or
$R^1$ and $R^2$ together stand for alkylenedioxy which is optionally substituted by halogen,
$R^3$ stands for alkyl and
$R^4$ stands for alkyl which is substituted by fluorine and optionally in addition by chlorine and/or bromine.

The corresponding isocyanates of the formula

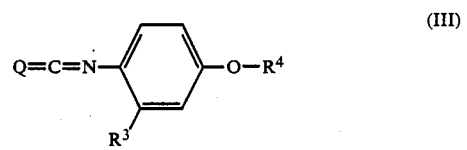

are also new.

11 Claims, No Drawings

FURAZANYLUREA ACARICIDES

The invention relates to new 1-arylfurazanyl-3-(2-alkyl-4-halogenoalkoxy-phenyl)-(thio)ureas, processes and new intermediates for their preparation, and their use as pesticides, in particular acaricides.

It has already been disclosed that certain substituted furazans, such as, for example, 1-(4-phenyl-1,2,5-oxadiazol-3-yl)-3-(4-trifluoromethoxy-phenyl)-urea and 1-(4-phenyl-1,2,5-oxadiazol-3-yl)-3-(4-(2-chloro-1,1,2-trifluoro-ethoxy)-phenyl)-urea, exhibit acaricidal properties (cf. EP-A 132,680).

The new 1-arylfurazanyl-3-(2-alkyl-4-halogenoalkoxy-phenyl)-(thio)ureas of the general formula (I)

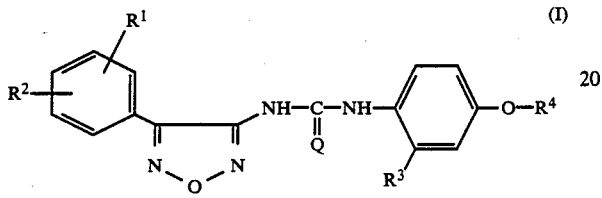

in which
Q stands for oxygen or sulphur,
$R^1$ stands for hydrogen, halogen, alkyl, halogenoalkyl, alkoxy, halogenoalkoxy, alkylthio or halogenoalkyl-thio and
$R^2$ stands for hydrogen, halogen, alkyl or alkoxy, or
$R^1$ and $R^2$ together stand for alkylenedioxy which is optionally substituted by halogen,
$R^3$ stands for alkyl and
$R^4$ stands for alkyl which is substituted by fluorine and optionally in addition by chlorine and/or bromine, have now been found.

Furthermore, it has been found that the new 1-arylfurazanyl-3-(2-alkyl-4-halogenoalkoxy-phenyl)-(thio)-ureas of the general formula (I) are obtained when (a) 3-amino-4-aryl-1,2,5-oxadiazoles ("arylfurazanyl-amines") of the general formula (II),

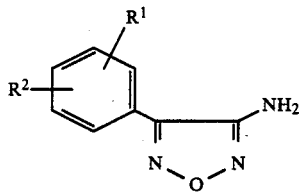

in which
$R^1$ and $R^2$ have the abovementioned meanings, are reacted with 2-alkyl-4-halogenoalkoxy-phenyl-iso(thio)cyanates of the general formula (III)

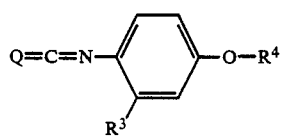

in which
Q, $R^3$ and $R^4$ have the abovementioned meanings, if appropriate in the presence of catalysts and if appropriate in the presence of diluents, or (b) 3-iso(thio)cyanato-4-aryl-1,2,5-oxadiazoles ("arylfurazanyliso(thio)cyanates") of the general formula (IV)

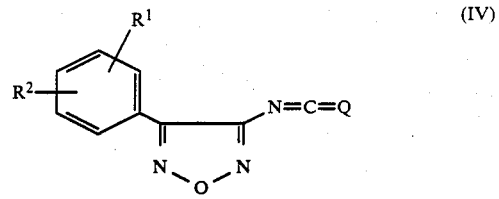

in which
Q, $R^1$ and $R^2$ have the abovementioned meanings, are reacted with 2-alkyl-4-halogenoalkoxy-anilines of the general formula (V)

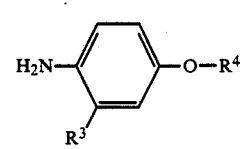

in which
$R^3$ and $R^4$ have the above mentioned meanings, if appropriate in the presence of catalysts and if appropriate in the presence of diluents.

Alkyl $R^1$, $R^2$, $R^3$ and $R^4$ is straight-chain or branched and preferably contains 1 to 6, in particular 1 to 4, carbon atoms. Examples which may be mentioned are methyl, ethyl, n-propyl, isopropyl, n-butyl, isobutyl, sec-butyl and tert-butyl. Methyl and ethyl are particularly preferred.

Halogenoalkyl $R^1$ is straight-chain or branched and preferably contains 1 to 4, in particular 1 or 2, carbon atoms and preferably 1 to 3 halogen atoms, the halogen atoms being identical or different and fluorine, chlorine or bromine, in particular fluorine, preferably standing as halogen atoms. Examples which may be mentioned are difluoromethyl, trifluoromethyl, chlorodifluoromethyl and fluorodichloromethyl. Trifluoromethyl is particularly preferred.

Alkoxy and alkylthio $R^1$ and alkoxy $R^2$ contain straight-chain or branched alkyl preferably having 1 to 6, in particular 1 to 4, carbon atoms in the alkyl moiety. Examples which may be mentioned are methoxy, ethoxy, n-propoxy, isopropoxy, n-butoxy, isobutoxy, sec-butoxy, methylthio, ethylthio, n-propylthio, isopropylthio, n-butylthio, isobutylthio and sec-butylthio. Methoxy is particularly preferred.

Halogenoalkoxy and halogenoalkylthio $R^1$ contains straight-chain or branched alkyl preferably having 1 to 4, in particular 1 to 3, carbon atoms and preferably 1 to 5, in particular 2 to 4, halogen atoms in the alkyl moiety, the halogen atoms being identical or different and fluorine, chlorine or bromine, in particular fluorine, preferably standing as halogen atoms. Examples which may be mentioned are difluoromethoxy, trifluoromethoxy, tetrafluoroethoxy, chlorotrifluoroethoxy, difluoromethylthio, trifluoromethylthio, chlorodifluoromethylthio, fluorodichloromethylthio, tetrafluoroethylthio, fluorodichloromethylthio, tetrafluoroethylthio and chlorotrifluoroethylthio. Trifluoromethoxy and trifluoromethylthio are particularly preferred.

In the definition of $R^1$ and $R^2$, alkylenedioxy preferably contains 1 to 3, in particular 1 to 2, carbon atoms and may contain straight-chain or branched alkylene which is optionally substituted by halogen (preferably fluorine and/or chlorine). Examples which may be mentioned are methylenedioxy, difluoromethylenedioxy, dimethylenedioxy, trifluorodimethylenedioxy, tetrafluorodimethylenedioxy and chlorotrifluorodimethylenedioxy.

Unless otherwise indicated, halogen stands for fluorine, chlorine, bromine or iodine, preferably for fluorine or chlorine.

Q preferably stands for oxygen.

The new compounds of the general formula (I) have properties which permit their use as pesticides; they show good insecticidal action and are distinguished in particular by very good acaricidal activity.

Preferred new 1-arylfurazanyl-3-(2-alkyl-4-halogenoalkoxy-phenyl)-(thio)ureas of the formula (I) are those in which Q stands for oxygen or sulphur, $R^1$ stands for hydrogen, halogen, $C_1$-$C_6$-alkyl, $C_1$-$C_4$-halogenoalkyl, $C_1$-$C_6$-alkoxy, $C_1$-$C_4$-halogenoalkoxy, $C_1$-$C_6$-alkylthio or for $C_1$-$C_4$-halogenoalkylthio, and $R^2$ stands for hydrogen, halogen, $C_1$-$C_4$-alkyl or $C_1$-$C_4$-alkoxy, or $R^1$ and $R^2$ together stand for $C_1$-$C_3$-alkylenedioxy which is optionally substituted by fluorine and/or chlorine, $R^3$ stands for $C_1$-$C_4$-alkyl, and $R^4$ stands for $C_1$-$C_6$-alkyl which is substituted by fluorine and optionally in addition by chlorine and/or bromine.

Particularly preferred new 1-arylfurazanyl-3-(2-alkyl-4-halogenoalkoxy-phenyl)-(thio)ureas of the formula (I) are those in which Q stands for oxygen or sulphur (preferably oxygen), $R^1$ stands for hydrogen, fluorine, chlorine, bromine, $C_1$-$C_4$-alkyl, for methyl which is substituted by fluorine and/or chlorine, for $C_1$-$C_4$-alkoxy, for $C_1$-$C_3$-alkoxy which is substituted by fluorine and/or chlorine, for $C_1$-$C_4$-alkylthio or for $C_1$-$C_4$-alkylthio which is substituted for fluorine and/or chlorine, and $R^2$ stands for hydrogen, fluorine, chlorine, bromine, methyl or methoxy, or $R^1$ and $R^2$ together stand for $C_1$-$C_2$-alkylenedioxy which is optionally substituted for fluorine and/or chlorine, $R^3$ stands for methyl, and $R^4$ stands for $C_1$-$C_4$-alkyl which is substituted by fluorine and optionally in addition by chlorine.

Very particularly preferred compounds of the formula (I) are those in which $R^1$ stands for hydrogen, fluorine, chlorine, methyl, trifluoromethyl or methoxy, $R^2$ stands for hydrogen, fluorine or chlorine, $R^3$ stands for methyl, $R^4$ stands for —$CF_3$ or —$CF_2CHFCl$, and Q stands for oxygen or sulphur (preferably oxygen).

Examples of compounds of the formula (I) are listed in Table 1 below and also in the Preparation Examples

TABLE 1

Examples of the compounds of the formula (I)

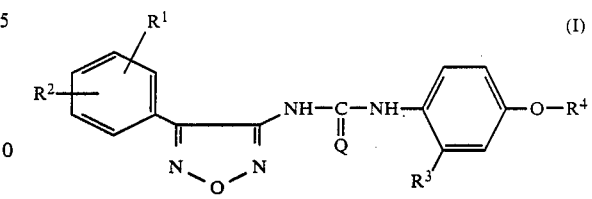

| Q | $R^1$ | $R^2$ | $R^3$ | $R^4$ |
|---|-------|-------|-------|-------|
| O | H | H | $CH_3$ | $CHF_2$ |
| S | H | H | $CH_3$ | $CHF_2$ |
| O | 2-Br | H | $CH_3$ | $CF_3$ |
| O | 2-Cl | 4-Cl | $CH_3$ | $CF_3$ |
| O | 2-F | 6-F | $CH_3$ | $CF_3$ |
| O | 2-$CH_3$ | H | $CH_3$ | $CF_3$ |
| O | 4-$CF_3$ | H | $CH_3$ | $CF_3$ |
| O | 4-$OCH_3$ | H | $CH_3$ | $CHF_2$ |
| O | 3-$OCH_3$ | 4-$OCH_3$ | $CH_3$ | $CF_3$ |
| O | 4-$SCH_3$ | H | $CH_3$ | $CF_3$ |
| O | 4-$OCF_3$ | H | $CH_3$ | $CF_3$ |
| O | 4-$SCF_3$ | H | $CH_3$ | $CF_3$ |
| O | H | H | $CH_3$ | $CF_2CHF_2$ |
| O | H | H | $CH_3$ | $CH_2CF_3$ |
| O | H | H | $CH_3$ | $CF_2CF_3$ |
| O | H | H | $C_2H_5$ | $CF_2CHFCl$ |
| O | H | H | $CH_3$ | $CF_2CHCl_2$ |
| O | H | H | $CH_3$ | $CF_2CCl_3$ |
| O | H | H | $CH_3$ | $CF_2CHBr_2$ |
| O | H | H | $CH_3$ | $CF_2CHFBr$ |
| O | H | H | $CH_3$ | $CF_2CHFCF_3$ |
| S | H | H | $CH_3$ | $CF_2CHFCF_3$ |
| S | H | H | $CH_3$ | $CH_2CF_3$ |
| O | H | H | $CH_3$ | $CF_2Cl$ |
| S | H | H | $CH_3$ | $CF_2Cl$ |

If, according to process variant (a), 3-amino-4-phenyl-1,2,5-oxadiazole and 2-methyl-4-difluoromethoxyphenyl isocyanate are used as starting substances, the course of the reaction may be represented by the following equation:

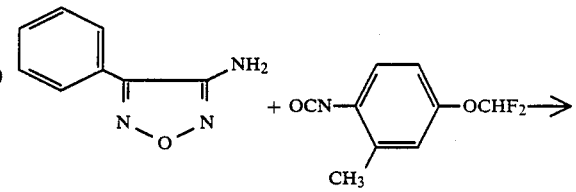

If, according to process variant (b), 3-isocyanato-4-phenyl-1,2,5-oxadiazole and 2-methyl-4-trifluoromethoxyaniline are used as starting substances, the course of the reaction may be represented by the following equation:

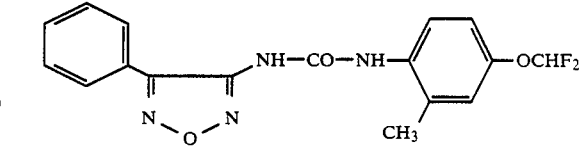

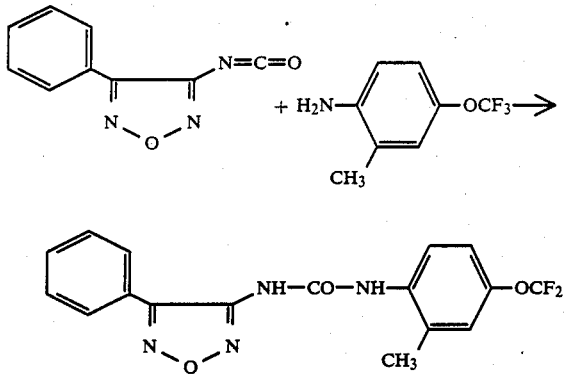

The 3-amino-4-aryl-1,2,5-oxadiazoles of the formula (II) to be used as the starting substances are known and/or can be prepared by processes which are known per se (cf. J. Prakt. Chem. 315 (1973), 791–795; U.S. Pat. No. 3,594,388).

The compounds of the formula (II) can be converted to give compounds of the formula (IV) by customary methods, for example by reaction with phosgene or thiophosgene in diluents, such as, for example, toluene, o-dichlorobenzene and/or pyridine, at temperatures between 20° C. and 200° C. (cf. EP-A 132,680, DE-OS (German Published Specification) 3,409,887).

The 2-alkyl-4-halogenoalkoxy-anilines of the formula (V) furthermore to be used as starting substances are likewise known and/or can be prepared by processes which are known per se (cf. DE-OS (German Published Specification) 2,113,978, DE-OS (German Published Specification) 3,135,926, EP-A 136,974, U.S. Pat. No. 3,937,726 and U.S. Pat. No. 4,013.452).

The compounds of the formula (V) can be converted to give compounds of the formula (III) by customary methods, for example by reaction with phosgene or thiophosgene in diluents, such as, for example, toluene, o-dichlorobenzene and/or pyridine, at temperatures between 20° C. and 200° C., (cf. Angew. Chem. 89 (1977), 979–804).

The compounds of the formula (III) which are obtained in this manner were not known hitherto from the literature.

Thus, the new compounds of the formula (III) are also part of the present invention. The general and preferred definitions as indicated for the compounds of the formula (I) are valid for the definitions of the radicals in the compounds of the formula (III), accordingly.

Suitable diluents for the process according to the invention (variants (a) and (b) are virtually all inert organic solvents. These preferably include aliphatic and aromatic hydrocarbons, optionally halogenated, such as pentane, hexane, heptane, cyclohexane, petroleum ether, benzine, ligroin, benzene, toluene, xylene, dichloromethane, dichloroethane, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethyl acetamide and N-methylpyrrolidone, and also tetramethylenesulphone.

Catalysts which can be used for the reaction in accordance with process variants (a) and (b) are preferably tertiary amines, such as triethylamine and 1,4-diazabicyclo-[2,2,2]-octane, and also organic tin compounds, such as, for example, dibutyltin dilaurate. In general, the addition of the catalyst does not provide any advantages.

The reaction temperature may be varied within a relatively wide range. In general, process variant (a) is carried out between 20° C. and 180° C., preferably between 40° C. and 120° C., and process variant (b) is carried out between 20° C. and 200° C., preferably between 60° C. and 190° C. In general, the process variants according to the invention are carried out under atmospheric pressure.

For carrying out the process variants according to the invention, the starting substances are are generally employed in approximately equimolar amounts. An excess of one or the other reaction component does not provide substantial advantages. Preferably, 0.6 to 1.5 moles, in particular 0.8 to 1.2 moles, of the compound of the formula (III) or (V) is employed per mol of the compound of the formula (II) or (IV), respectively.

The reaction products are worked up by customary methods, for example by filtering off the precipitated product with suction or by removing undesired by-products from the reaction mixture by dissolving them. The reaction products are characterized by their melting points.

The active compounds are suitable for combating animal pests, preferably arthropods and nematodes, particularly insects and arachnida, encountered in agriculture, forestry, the protection of stored products and materials, and also in the hygiene sector. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanige-* rum, *Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia Litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamenis, Antho nomus* spp., Sitophilus spp., *Otiorrhynchus sulcatus, Cosmopolites sordidus, Ceuthorrhynchus assimiles, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophilia melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The compounds of the formula (I) according to the invention are distinguished by a good insecticidal and, in particular, by a good acaricidal activity, in particular against eggs (ovicidal action) and against the larvae (larvicidal action) of the pests.

On application as acaricides, in particular, they show excellent action against eggs and larvae of the common spider mite (*Tetranychus urticae*) and fruit tree red spider mite (*Panonychus ulmi*), and have very good action against virtually all development stages of spider mites.

The active compounds can be converted, depending on their particular physical and/or chemical properties, into the customary formulations, such as solutions, emulsions, suspensions, powders, foams, pastes, granules, aerosols, natural and synthetic materials impregnated with active compound, very fine capsules in polymeric substances and in coating compositions for seed, and furthermore into formulations with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant those liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorilonite or diatomaceous earth, and ground synthetic minerals, such as finely divided silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inoganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 90%.

The active compounds can be present in their commercially available formulations and in the use forms, prepared from these formulations, as a mixture with other active compounds, such as insecticides, baits, acaricides, nematicides, fungicides, growth-regulating substances, or herbicides. The insecticides include, for example phosphates, carbamates, carboxylates, chlorinated hydrocarbons, phenylureas, substances produced by microorganisms, among others.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The content of active compound of the use forms prepared from the commercially available formulations can vary within wide ranges. The concentration of active compound of the use forms can be 0.0000001 to 95% by weight of active compound, preferably between 0.0001 and 1% by weight.

The application is carried out in a customary manner to suit the use forms.

When applied against pests in the hygiene field and against pests of stored products, the active compounds are distinguished by excellent residual action on wood and clay, and by a good stability to alkali on limed substrates.

Unless indicated otherwise, all percentages in the present text refer to percentages by weight.

Preparation Examples

EXAMPLE 1

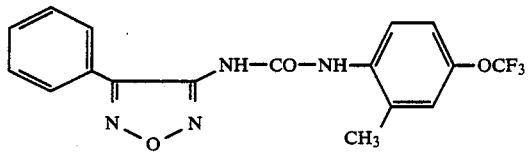

(Process variant (b))

1.87 g (0.01 mol) of 3-isocyanato-4-phenyl-1,2,5-oxadiazole, dissolved in 10 ml of dry toluene, is added to a solution of 1.91 g (0.01 mol) of 2-methyl-4-trifluoromethoxy-aniline in 40 ml of dry toluene, at 60° C. with the exclusion of moisture. The batch is stirred for half an hour at 80° C. and then concentrated in vacuo. The product precipitated is sucked in and washed with petroleum ether.

3.5 g (92.5% of theory) of 1-[(2-methyl-4-trifluoromethoxy)-phenyl]-3-(4-phenyl-1,2,5-oxadiazol-3-yl)-urea of melting point 198° C. are obtained.

Process variant (a))

9.03 g (0.042 mol) of 2-methyl-4-trifluoromethoxy-phenylisocyanate are added to a solution of 6.44 g (0.44 mol) of 3-amino-4-phenyl-1,2,5-oxadiazole in 20 ml of dry dimethylformamide. The batch is stirred for two hours at 100° C.; the solvent is then removed in vacuo by evaporation, the residue is dissolved in boiling toluene, a small amount of petroleum ether is added to the mixture, the mixture is cooled, and the produce precipitated in the form of crystals is isolated by filtering off with suction.

11.3 g of 1-(4-phenyl-1,2,5-oxadiazol-3-yl)-3-(2-methyl-4-trifluoromethoxy-phenyl)-urea with a content of 74%, by HPLC, are obtained.

In analogy with Example 1 and in accordance with the general description of process variants (a) and (b), the compounds of the formula (I) listed in the following Table 2 can be prepared.

TABLE 2:

Examples of the compounds of the formula (I)

| Example No. | Q | $R^1$ | $R^2$ | $R^3$ | $R^4$ | Melting point (°C.) |
|---|---|---|---|---|---|---|
| 2 | O | 4-F | H | $CH_3$ | $CF_3$ | 190 |
| 3 | O | 4-Cl | H | $CH_3$ | $CF_3$ | 216 |
| 4 | O | 2-Cl | H | $CH_3$ | $CF_3$ | 207 |
| 5 | O | 3-$CF_3$ | H | $CH_3$ | $CF_3$ | 207 |
| 6 | O | 2-F | 4-F | $CH_3$ | $CF_3$ | 204 |
| 7 | O | 4-$CH_3$ | H | $CH_3$ | $CF_3$ | 196 |
| 8 | O | 4-$OCH_3$ | H | $CH_3$ | $CF_3$ | 196 |
| 9 | O | 3-Cl | 4-Cl | $CH_3$ | $CF_3$ | 200 |
| 10 | O | 3-O—$CH_2$—O—4 | | $CH_3$ | $CF_3$ | 196 |
| 11 | O | 2-F | H | $CH_3$ | $CF_3$ | 216 |
| 12 | S | H | H | $CH_3$ | $CF_3$ | 126 |
| 13 | O | H | H | $CH_3$ | $CF_2CHFCl$ | 200 |
| 14 | O | 4-Cl | H | $CH_3$ | $CF_2CHFCl$ | 203 |
| 15 | O | 2-Cl | H | $CH_3$ | $CF_2CHFCl$ | 204 |
| 16 | O | 2-F | H | $CH_3$ | $CF_2CHFCl$ | 202 |
| 17 | O | 4-F | H | $CH_3$ | $CF_2CHFCl$ | 181 |
| 18 | S | 2-Cl | H | $CH_3$ | $CF_2CHFCl$ | 128 |
| 19 | O | 4-Br | H | $CH_3$ | $CF_2CHFCl$ | 205 |
| 20 | O | 3-$CF_3$ | H | $CH_3$ | $CF_2CHFCl$ | 217 |
| 21 | O | 4-$CH_3$ | H | $CH_3$ | $CF_2CHFCl$ | 168 |
| 22 | O | 4-$OCH_3$ | H | $CH_3$ | $CF_2CHFCl$ | 169 |
| 23 | O | 3-Cl | 4-Cl | $CH_3$ | $CF_2CHFCl$ | 203 |
| 24 | O | 2-F | 4-F | $CH_3$ | $CF_2CHFCl$ | 198 |
| 25 | O | 3-O—$CH_2$—O—4 | | $CH_3$ | $CF_2CHFCl$ | 188 |

Compounds of the formula (III)

Preparation Example

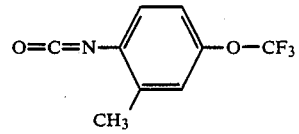

50 g of phosgene are passed into 500 ml of dry toluene at 0°–5° C. 95.5 of 2-methyl-4-trifluoromethoxyaniline in 200 ml of dry toluene are then added dropwise at the same temperature. The batch is refluxed for 3 hours, with simultaneous introduction of phosgene. Excess phosgene is then flushed out with nitrogen. The solvent is distilled off, and the liquid residue is distilled.

93 g (85.5% of theory) of 2-methyl-4-trifluoromethoxy-phenylisocyanant of boiling point B.p.$_2$ 54° C. and a refractive index of $n_D^{20}$1.4626 are obtained.

The other isocanates are prepared in the same manner, for example

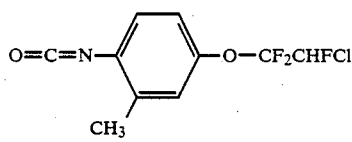

B.p.$_2$ = 102° C.
$n^{20}$ = 1.4855
Yield = 82% of theory

EXAMPLE A

Panonychus test

Solvent: 3 parts by weight of dimethylformamide
Emulsifier: 1 part by weight of alkylaryl polyglycol ether To produce an expedient preparation of active compound, 1 part by weight of active compound is mixed with the stated amount of solvent containing the stated amount of emulsifier, and the concentrate is diluted to the desired concentration with water.

Young plum trees (*Prunus myrobolana*) having a height of approximately 20 to 30 cm are sprayed with the preparation of active compound until dripping wet. These young plum trees are heavily infested with all development stages of the fruit tree red spider mites (*Panonychus ulmi*).

After the times indicated, the activity is determined by counting the surviving animals. The degree of action thus obtained is given in %. 100% means that all spider mites have been killed, and 0% means that none have been killed.

In this test, the compounds of Preparation Examples (1) and (13) showed a degree of destruction of 100% after 14 days, at an illustrative concentration of 0.00016%.

EXAMPLE B

Panonychus test

Solvent: 3 parts by weight of dimethylformamide
Emulsifier: 1 part by weight of alkylaryl polyglycol ether To produce an expedient preparation of active compound, 1 part by weight of active compound is mixed with the stated amount of solvent containing the stated amount of emulsifier, and the concentrate is diluted to the desired concentration with water.

Young plum trees (*Prunus myrobolana*) of 20 to 30 cm which are infested with about 100 eggs of the fruit tree red spider mite (*Panonychus ulmi*) are treated by spraying with the active compound preparation of the desired concentration.

After the times indicated, the activity is determined by counting the surviving animals. The action thus obtained is given in %. 100% means that all spider mites have been killed, and 0% means that none have been killed.

In this test, the compounds of Preparation Examples (1) and (13), for example, showed a degree of destruction of 100% after 12 days, at an illustrative concentration of 0.00016%.

EXAMPLE C

Tetranychus test

Solvent: 3 parts by weight of dimethylformamide
Emulsifier: 1 part by weight of alkylaryl polyglycol ether To produce an expedient preparation of active compound, 1 part by weight of active compound is mixed with the stated amount of solvent and the stated amount of emulsifier, and the concentrate is diluted to the desired concentration with water.

Bean plants (*Phaseolus vulgaris*) which are infested with about 100 eggs of the common spider mite (*Tetranychus urticae*) are treated by immersing them into the active compound preparation of the desired concentration.

Destruction, as a %, is determined after the desired time. Here, 100% means that all spider mites (eggs and development stages) have been killed, and 0% means that none have been killed.

In this test, the compounds of Preparation Examples (1) and (13) for example, showed a destruction of 100% after 12 days, at an illustrative concentration of 0.0008%.

EXAMPLE D

Test for egg sterility and inhibition of development of *Tetranychus urticae* (common spider mite)

Solvent: 3 parts by weight of dimethylformamide
Emulsifier: 1 part by weight of alkylaryl polyglycol ether To produce an expedient preparation of active compound, 1 part by weight of active compound is mixed with the stated amount of solvent and the stated amount of emulsifier, and the concentrate is diluted to the desired concentration with water.

The leaves of a bean plant (*Phaseolus vulgaris*) are immersed in the active compound preparation of the appropriate concentration. After the active compound preparation has dried on, the leaves are infested with female spider mites for about 16 hours, for laying eggs (about 50 eggs/replication). Destruction in % results from the sum of sterile and/or destroyed eggs and the destroyed larvae, nymphae and dormant stages of a generation, based on the number of laid eggs. Here, 100% means that all animals have been destroyed, 0% means that none of the animals have been destroyed.

In this test, the compounds of the Preparation Examples (1), (11), (13), (14), (16) and (17), for example, showed a destruction of 100% after 12 days, at an illustrative concentration of 0.001%.

It will be appreciated that the instant specification and claims are set forth by way of illustration and not limitation, and that various modifications and changes may be made without departing from the spirit and scope of the present invention.

What is claimed is:

1. A 1-arylfurazanyl-3-(2-alkyl-4-halogenoalkoxyphenyl)-(thio)urea of the formula

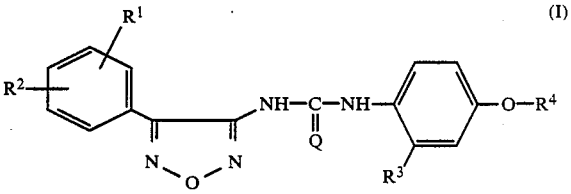

in which
Q stands for oxygen or sulphur,
$R^1$ stands for hydrogen, halogen, $C_1$-$C_6$-alkyl, $C_1$-$C_4$-halogenoalkyl, $C_1$-$C_6$-alkoxy, $C_1$-$C_4$-halogenoalkoxy, $C_1$-$C_6$-alkylthio or for $C_1$-$C_4$-halogenoalkylthio, and
$R^2$ stands for hydrogen, halogen, $C_1$-$C_4$-alkyl or $C_1$-$C_4$-alkoxy, or
$R^1$ and $R^2$ together stand for $C_1$-$C_3$-alkylene-dioxy which is optionally substituted by fluorine and/or chlorine, $R^3$ stands for $C_1$–$C_4$-alkyl, and $R^4$ stands for $C_1$–$C_6$-alkyl which is substituted by fluorine and optionally in addition by chlorine and/or bromine.

2. A compound according to claim 1, in which

Q stands for oxygen or sulphur, $R^1$ stands for hydrogen, fluorine, chlorine, bromine, $C_1$–$C_4$-alkyl, for methyl which is substituted by fluorine and/or chlorine, for $C_1$–$C_4$-alkoxy, for $C_1$–$C_3$-alkoxy which is substituted by fluorine and/or chlorine, for $C_1$–$C_4$-alkylthio or for $C_1$–$C_4$-alkylthio which is substituted by fluorine and/or chlorine, and $R^2$ stands for hydrogen, fluorine, chlorine, bromine, methyl or methoxy, or $R^1$ and $R^2$ together stand for $C_1$–$C_2$-alkylenedioxy which is optionally substituted by fluorine and/or chlorine, $R^3$ stands for methyl, and $R^4$ stands for $C_1$–$C_4$-alkyl which is substituted by fluorine and optionally in addition by chlorine.

3. A compound according to claim 1, in which

Q stands for oxygen, $R^1$ stands for hydrogen, fluorine, chlorine, methyl, trifluoromethyl or methoxy, $R^2$ stands for hydrogen, fluorine or chlorine, $R^3$ stands for methyl, and $R^4$ stands for —$CF_3$ or —$CF_2CHFCl$.

4. A compound according to claim 1, wherein such compound is 1-(4-phenyl-1,2,5-oxadiazol-3-yl)-3-(2-methyl-4-trifluoromethoxy-phenyl)-urea of the formula

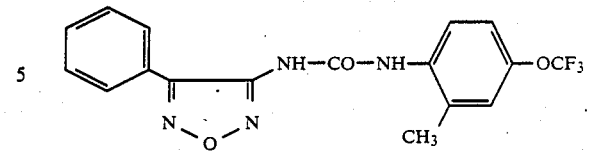

5. A compound according to claim 1, wherein such compound is 1-(4-phenyl-1,2,5-oxadiazol-3-yl)-3-[2-methyl-4-(2-chloro-1,1,2-trifluoro-ethoxy)-phenyl]-urea of the formula

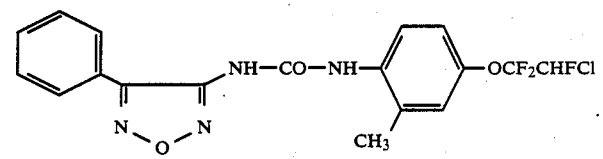

6. A compound according to claim 1, wherein such compound is 1-[4-(4-chloro-phenyl)-1,2,5-oxadiazol-3-yl]-3-[2-methyl-4-(2-chloro-1,1,2-trifluoro-ethoxy)-phenyl]-urea of the formula

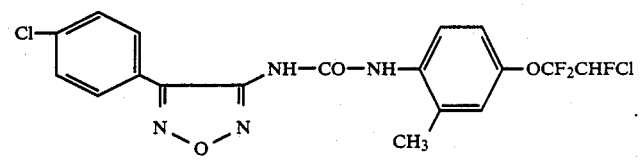

7. A compound according to claim 1, wherein such compound is 1-[4-(2-fluoro-phenyl)-1,2,5-oxadiazol-3-yl]-3-[2-methyl-4-(2-chloro-1,1,2-trifluoro-ethoxy)-phenyl]-urea of the formula

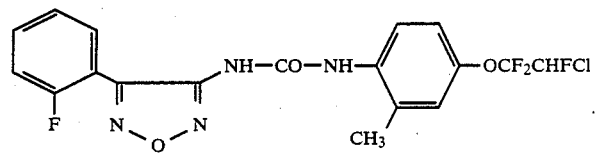

8. A compound according to claim 1, wherein such compound is 1-[4-(4-fluoro-phenyl)-1,3,5-oxadiazol-3-yl]-3-[2-methyl-4-(2-chloro-1,1,2-trifluoro-ethoxy)-phenyl]-urea of the formula

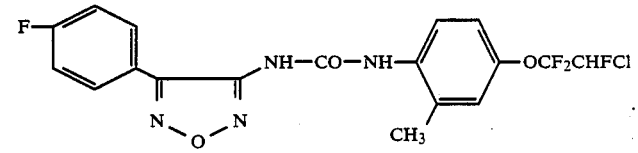

9. An acaricidal composition comprising an acaricidially effective amount of a compound according to claim 1 and a diluent.

10. A method of combating acarids which comprises applying to such acarids an acaricidally effective amount of a compound according to claim 1.

11. The method according to claim 10, wherein such compound is 1-(4-phenyl-1,2,5-oxadiazol-3-yl)-3-(2-methyl-4-trifluoromethoxy-phenyl)-urea, 1-(4-phenyl-1,2,5-oxadiazol-3-yl)-3-[2-methyl-4-(2-chloro-1,1,2-trifluoro-ethoxy)-phenyl]-urea, 1-[4-(4-chloro-phenyl)-1,2,5-oxadiazol-3-yl]-3-[2-(methyl-4-(2-chloro-1,1,2-trifluoro-ethoxy)-phenyl]-urea,
1-[4-(2-fluoro-phenyl)-1,2,5-oxadiazol-3-yl-3-[2-methyl-4-(2-chloro-1,1,2-trifluoro-ethoxy)-phenyl]-urea, or
1-[4-(4-fluoro-phenyl)-1,3,5-oxadiazol-3-yl]-3-[2-methyl-4-(2-chloro-1,1,2-trifluoro-ethoxy)-phenyl]-urea.

* * * * *

UNITED STATES PATENT AND TRADEMARK OFFICE
CERTIFICATE OF CORRECTION

PATENT NO. : 4,886,823

DATED : December 12, 1989

INVENTOR(S) : Sirrenberg et al.

It is certified that error appears in the above-identified patent and that said Letters Patent is hereby corrected as shown below:

Title Page     Add-- OTHER PUBLICATIONS : Chemical Abstracts, Vol. 105, 1986, Page 620, Abstract 24073p. --

Col. 16, claim 11 line 1     After " -[2- " delete " ( "

Col. 16, claim 11 line 3     After " 3-yl " insert -- ) --

Signed and Sealed this

Seventh Day of July, 1992

Attest:

DOUGLAS B. COMER

Attesting Officer     Acting Commissioner of Patents and Trademarks